US012653614B2

(12) United States Patent (10) Patent No.: US 12,653,614 B2

Clayman et al. (45) Date of Patent: Jun. 16, 2026

(54) MODULAR WIRELESS LARGE BORE VACUUM UNIVERSAL ENDOSCOPE AND VACUUMSCOPE

(71) Applicant: THE REGENTS OF THE UNIVERSITY OF CALIFORNIA, Oakland, CA (US)

(72) Inventors: Ralph V. Clayman, Orange, CA (US); Kamaljot S. Kaler, Orange, CA (US); Andrew Emon Heidari, Irvine, CA (US); Roshan M. Patel, Irvine, CA (US); Jamie Landman, Orange, CA (US); Pengbo Jiang, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 17/738,758

(22) Filed: May 6, 2022

(65) Prior Publication Data

US 2022/0265350 A1 Aug. 25, 2022

Related U.S. Application Data

(63) Continuation-in-part of application No. 16/421,061, filed on May 23, 2019, now abandoned.

(Continued)

(51) Int. Cl.
*A61B 18/26* (2006.01)
*A61B 1/00* (2006.01)
(Continued)

(52) U.S. Cl.
CPC .......... *A61B 18/26* (2013.01); *A61B 1/00087* (2013.01); *A61B 1/01* (2013.01);
(Continued)

(58) Field of Classification Search
CPC . A61B 1/307; A61B 1/00094; A61B 1/00051; A61B 1/00057; A61B 1/015;
(Continued)

(56) References Cited

U.S. PATENT DOCUMENTS

| | | | | |
|---|---|---|---|---|
| 10,660,510 B2 * | 5/2020 | Campisi | ................. | A61M 1/89 |
| 2006/0173244 A1 * | 8/2006 | Boulais | ................. | A61B 1/015 |
| | | | | 600/156 |

(Continued)

OTHER PUBLICATIONS

USPTO, "Non-Final Office Action", issued in connection with U.S. Appl. No. 18/169,646, dated Jul. 18, 2025, 16 pages.

(Continued)

*Primary Examiner* — Michael J Carey
*Assistant Examiner* — Megan Elizabeth Monahan
(74) *Attorney, Agent, or Firm* — NGUYEN TARBET IP LAW

(57) ABSTRACT

The present technology relates to ureteroscopy, laser ablation of ureteral and renal stone, capture and removal of stone fragments. In one embodiment, the device includes an optical instrument operably connected to a large vacuum channel that is about 1.5 mm to about 8.0 mm in width. In another embodiment, the device includes two single-time use disposable or potentially reusable units, such as a large vacuum endoscope removal tip and a wireless and modular battery-powered handpiece.

12 Claims, 5 Drawing Sheets

Related U.S. Application Data

(60) Provisional application No. 62/675,929, filed on May 24, 2018.

(51) Int. Cl.
| | |
|---|---|
| *A61B 1/01* | (2006.01) |
| *A61B 1/273* | (2006.01) |
| *A61B 1/307* | (2006.01) |
| *A61B 18/00* | (2006.01) |

(52) U.S. Cl.
CPC ............ *A61B 1/2736* (2013.01); *A61B 1/307* (2013.01); *A61B 2018/00517* (2013.01); *A61B 2217/005* (2013.01)

(58) Field of Classification Search
CPC ......... A61B 1/05; A61B 1/00087; A61B 1/01; A61B 1/2736; A61B 2217/005; A61B 2018/00517; A61B 18/26
See application file for complete search history.

(56) References Cited

U.S. PATENT DOCUMENTS

| | | | | |
|---|---|---|---|---|
| 2006/0252993 | A1* | 11/2006 | Freed ................... | A61B 1/0052 604/95.04 |
| 2007/0244353 | A1* | 10/2007 | Larsen ................... | A61B 1/126 600/105 |
| 2008/0188890 | A1 | 8/2008 | Weitzner et al. | |
| 2009/0036739 | A1* | 2/2009 | Hadani .............. | A61B 1/00105 600/121 |
| 2013/0131445 | A1 | 5/2013 | Zerfas et al. | |
| 2017/0215965 | A1* | 8/2017 | Harrah ................... | A61B 1/018 |
| 2017/0319776 | A1* | 11/2017 | Eisner ................... | A61M 39/22 |
| 2018/0014840 | A1 | 1/2018 | Panian | |
| 2018/0289394 | A1 | 10/2018 | Shah | |
| 2019/0038817 | A1 | 2/2019 | Forsberg et al. | |
| 2019/0082940 | A1 | 3/2019 | Igov | |
| 2020/0178945 | A1* | 6/2020 | Mandol .............. | A61B 1/00097 |
| 2020/0187768 | A1 | 6/2020 | Shelton et al. | |
| 2020/0315430 | A1* | 10/2020 | Ward-Booth ...... | A61B 1/00042 |
| 2020/0367736 | A1* | 11/2020 | Bawaadam ........ | A61B 1/00096 |
| 2021/0022759 | A1* | 1/2021 | Wan ................... | A61B 17/225 |
| 2022/0218367 | A1 | 7/2022 | Ghani et al. | |
| 2023/0042812 | A1 | 2/2023 | Walak et al. | |

OTHER PUBLICATIONS

USPTO, "Final Office Action", issued in connection with U.S. Appl. No. 18/169,646, dated Oct. 27, 2025, 15 pages.

* cited by examiner 1.2mm CMOS with
+200um space for fit

Vacuum Channel /w 6.94mm² area 2 mm stones

OD: 4.2 mm ~12F

Irrigation Channel

Laser Fiber
Or
Illumination 6.16mm ~ 18.6F

5mm

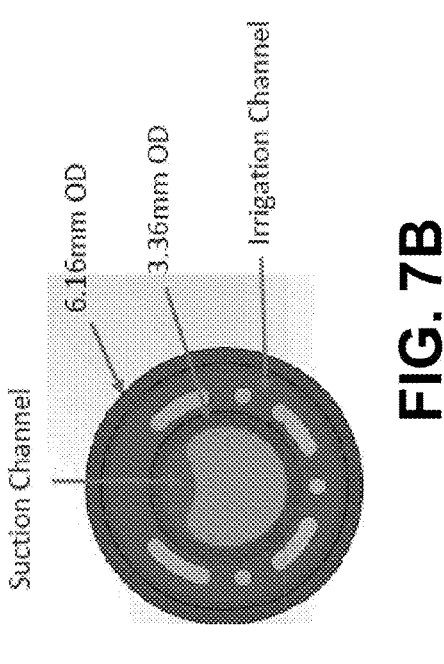
FIG. 7A
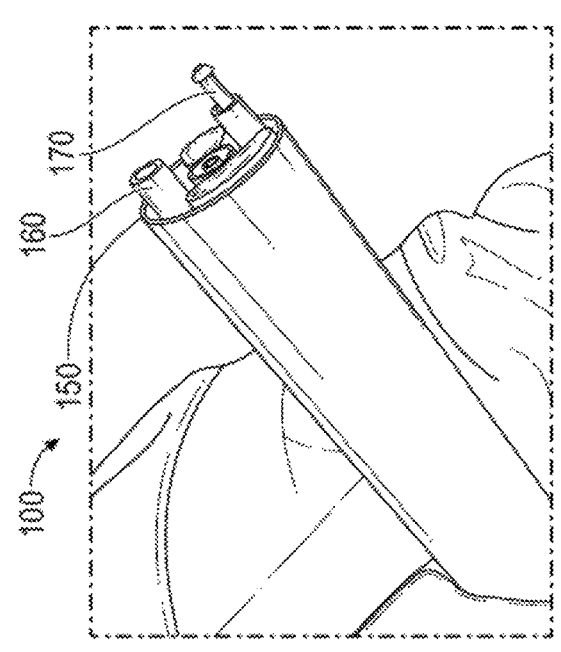
FIG. 7B
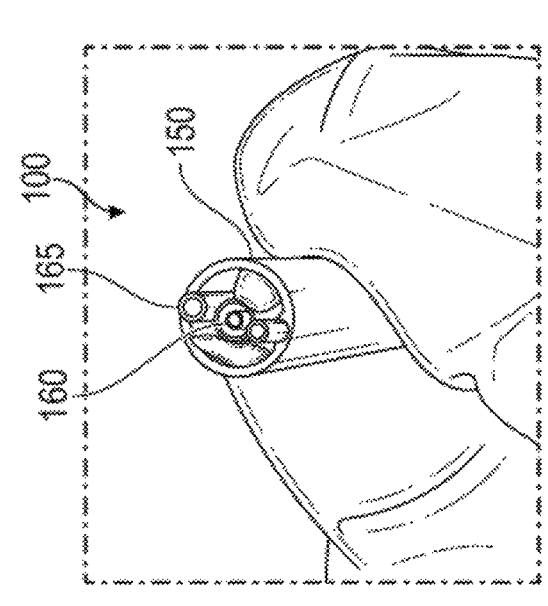
FIG. 8
FIG. 9

MODULAR WIRELESS LARGE BORE VACUUM UNIVERSAL ENDOSCOPE AND VACUUMSCOPE

CROSS-REFERENCES TO RELATED APPLICATIONS

This application is a continuation-in-part and claims benefit of U.S. patent application Ser. No. 16/421,061 filed May 23, 2019, which is a non-provisional and claims benefit of U.S. Patent Application No. 62/675,929 filed May 24, 2018, the specifications of which are incorporated herein in their entirety by reference.

FIELD OF THE INVENTION

The present disclosure relates to the medical field, and more specifically, ureteroscopy and surgical procedures.

BACKGROUND OF THE INVENTION

Nephrolithiasis, or the presence of renal calculi (kidney stones), is a common health problem across the globe with a prevalence of 10%. The prevalence is increasing given the current obesity epidemic. Nephrolithiasis may lead to persistent renal obstruction and permanent renal damage if left unresolved. On an annual basis, the cost to the USA economy ($10 billion) for the care and treatment of urolithiasis is greater than for any other urological condition. The failure to completely render the stone-bearing kidney free of all stone material results in a high rate of recurrent stone disease and further patient debility and expense.

Basket removal of kidney stone debris after laser lithotripsy fails to clear the smallest (<1-2 mm) remnants, leaving nidi for future stone formation. Comparing laser lithotripsy fibers, thulium produces significantly finer fragments (U 1000 microns) than holmium; debris too small for basket extraction.

The current acute treatment options for small renal/ureteral stones (i.e. </=7 mm in diameter) nephrolithiasis includes pain medication and hydration until the stone passes naturally or with pharmaceutical interventions that facilitate stone passage; approximately half of these small stones (<5 mm) will pass without the need for intervention. In instances where this approach fails or for larger stones, patients are treated with shock wave lithotripsy or ureteroscopic lithotripsy with electrohydraulic or laser probes as first-line management options, or percutaneous nephrolithotomy or laparoscopic stone removal when the stone is large (i.e. >1.5 cm). In contrast to shock wave lithotripsy, ureteroscopy is a less expensive procedure, yields higher stone-free rates, and can treat complicated, dense, or larger renal calculi up to 1.5 cm in diameter, in which shock wave lithotripsy may be unsuccessful. Recent advances in ureteroscopy have also reduced complication rates. Of note, the major drawback to both shock wave lithotripsy as well as ureteroscopy is that the stone clearance rate is no better than 50% on computed tomography (CT) scans; leaving even small stone fragments behind, puts the patient at high risk for recurrent stone disease within 2-4 years. Thus, the development of a novel ureteroscope/nephroscope capable of thoroughly removing all fragments from the kidney would be a welcome advance.

All publications herein are incorporated by reference to the same extent as if each publication or patent application was specifically and individually indicated to be incorporated by reference. The description herein includes information that may be useful in understanding the present invention. It is not an admission that any of the information provided herein is prior art or relevant to the presently claimed invention, or that any publication specifically or implicitly referenced is prior art.

BRIEF SUMMARY OF THE INVENTION

It is an objective of the present invention to provide devices and methods that allow for a novel ureteroscope/nephroscope capable of thoroughly removing all fragments of a kidney stone efficiently, as specified in the independent claims. Embodiments of the invention are given in the dependent claims. Embodiments of the present invention can be freely combined if they are not mutually exclusive.

Various embodiments include a device, comprising an optical instrument operably connected to a vacuum channel between 1.5 mm and 8.0 mm in width. In another embodiment, the vacuum channel is between 1.5 mm and 2.0 mm in width. In another embodiment, the optical instrument is an endoscope. In another embodiment, the optical instrument is a nephroscope. In another embodiment, the optical instrument is a ureteroscope. In another embodiment, the vacuum channel is the inner part of a vacuum scope. In another embodiment, the device further comprises a plurality of irrigation channels. In another embodiment, the plurality of irrigation channels is arrayed around the vacuum channel. In another embodiment, the plurality of irrigation channels includes channels that are straight and angled. In another embodiment, the vacuum channel is adapted to capture a stone between 1 mm and 3 mm. In another embodiment, the vacuum channel is adapted for a suction form of biopsy of a polyp and/or tumor in a subject. In another embodiment, the vacuum channel is adapted for suction in the colon or upper gastrointestinal tract of a subject. In another embodiment, the vacuum channel is a large bore central vacuum channel. In another embodiment, the vacuum channel is between 2.0 mm and 4.0 mm for use of the device as a ureteroscope. In another embodiment, the vacuum channel is between 6.0 mm to 8.0 mm for use of the device as a percutaneous nephroscope. In another embodiment, a visualization is achieved through an array of optical materials (e.g. deconstructed CMOS chip, LED lights, etc.) located around the vacuum channel. In another embodiment, a manipulation is achieved through a control mechanism located around the vacuum channel. In another embodiment, the manipulation further comprises a magnetic guidewire steering. In another embodiment, the device has a self-contained battery pack. In another embodiment, the device is enabled for wireless communication. For example, the device may be Bluetooth® and/or Wi-Fi® enabled, thereby eliminating all extraneous cords.

Other embodiments include a method of removing a biopsied tissue or stone particle or fragment thereof from an individual, comprising providing a device comprising an optical instrument operably connected to a vacuum channel that is about 1.5 mm to about 8.0 mm in width, and removing the biopsied tissue or stone particle or fragment thereof from the individual. In another embodiment, the biopsied tissue or stone particle or fragment thereof is removed as part of a bronchoscopy, gastroscopy, duodenoscopy, small bowel endoscopy, colonoscopy, arthroscopy, and/or laryngoscopy procedure. In another embodiment, the biopsied tissue or stone particle or fragment thereof is removed as part of a ureteroscopic and/or percutaneous nephrolithotomy procedure. In another embodiment, the vacuum channel is between 1.5 mm and 2.0 mm in width. In another embodiment, a visualization is achieved through an array of optical materials located around the vacuum channel.

Other embodiments include a method of performing a biopsy on a subject, comprising providing a device comprising an optical instrument operably connected to a vacuum channel that is about 1.5 mm to about 8.0 mm in width, and removing a biopsy sample from the subject. In another embodiment, the sample is a tumor and/or polyp. In another embodiment, the vacuum channel is between 2.0 mm and 8.0 mm.

Other features and advantages of the invention will become apparent from the following detailed description, taken in conjunction with the accompanying drawings, which illustrate, by way of example, various embodiments of the invention.

One of the unique and inventive technical features of the present invention is the implementation of a central bar disposed across a diameter of a vacuum channel. Without wishing to limit the invention to any theory or mechanism, it is believed that the technical feature of the present invention advantageously provides for precluded aspiration of fragments that would normally be too large to pass through. Furthermore, the inclusion of ports in the central bar allows for guide wires to be directed through to let the endoscope smoothly glide up a ureter, and the inclusion of light source components (LEDs), optical components (CMOS chips) allows users to laser, irrigate, and aspirate fragments simultaneously. None of the presently known prior references or work has the unique inventive technical feature of the present invention.

Furthermore, the inventive technical feature of the present invention contributed to a surprising result. For example, one skilled in the art would expect that a central bar design would greatly limit the size of fragments that can be passed through an endoscope as well as reduce the efficiency with which all fragments can be passed through. Surprisingly, the implementation of the central bar in the presently claimed invention increased the efficiency of fragment removal in terms of both size and rate of successful passage. Thus, the inventive technical feature of the present invention contributed to a surprising result.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWING(S)

The features and advantages of the present invention will become apparent from a consideration of the following detailed description presented in connection with the accompanying drawings in which:

FIG. 1A depicts, in accordance with embodiments herein, a modular wireless vacuum scope shown with a removal scope body and potentially wireless handpiece. In accordance with embodiments herein, the figure depicts a disposable (or reusable if desired) vacuum scope with connections for suction, fluid irrigation, laser fibers, and electrical contacts for CCD video as well as white light illumination, shown detached from the endoscope's handle.

FIG. 1B depicts, in accordance with embodiments herein, an example of a joystick magnetic guidewire steering mechanism that allows for 360-degree actuation of a ureteroscope, depicting both an outside view as well as an inside view of the mechanism. The figure depicts a mechanism with an interfacing mechanism 101 between a wire and ball joint joystick, which is further connected to magnets in a cylindrical track 102, which in turn are connected to the tip of the scope 103. This mechanism involves the use of a joystick thumb control that is attached to several guy wires in the handpiece body. In accordance with various embodiments herein, this control mechanism couples to detachable and disposable endoscope tips through magnets. From this interface, the magnets embedded in the endoscope back end may then translate the pulling force to the distal tip of the scope deflecting the scope in the direction that tension is applied.

Figures 5, 6A, 6B:
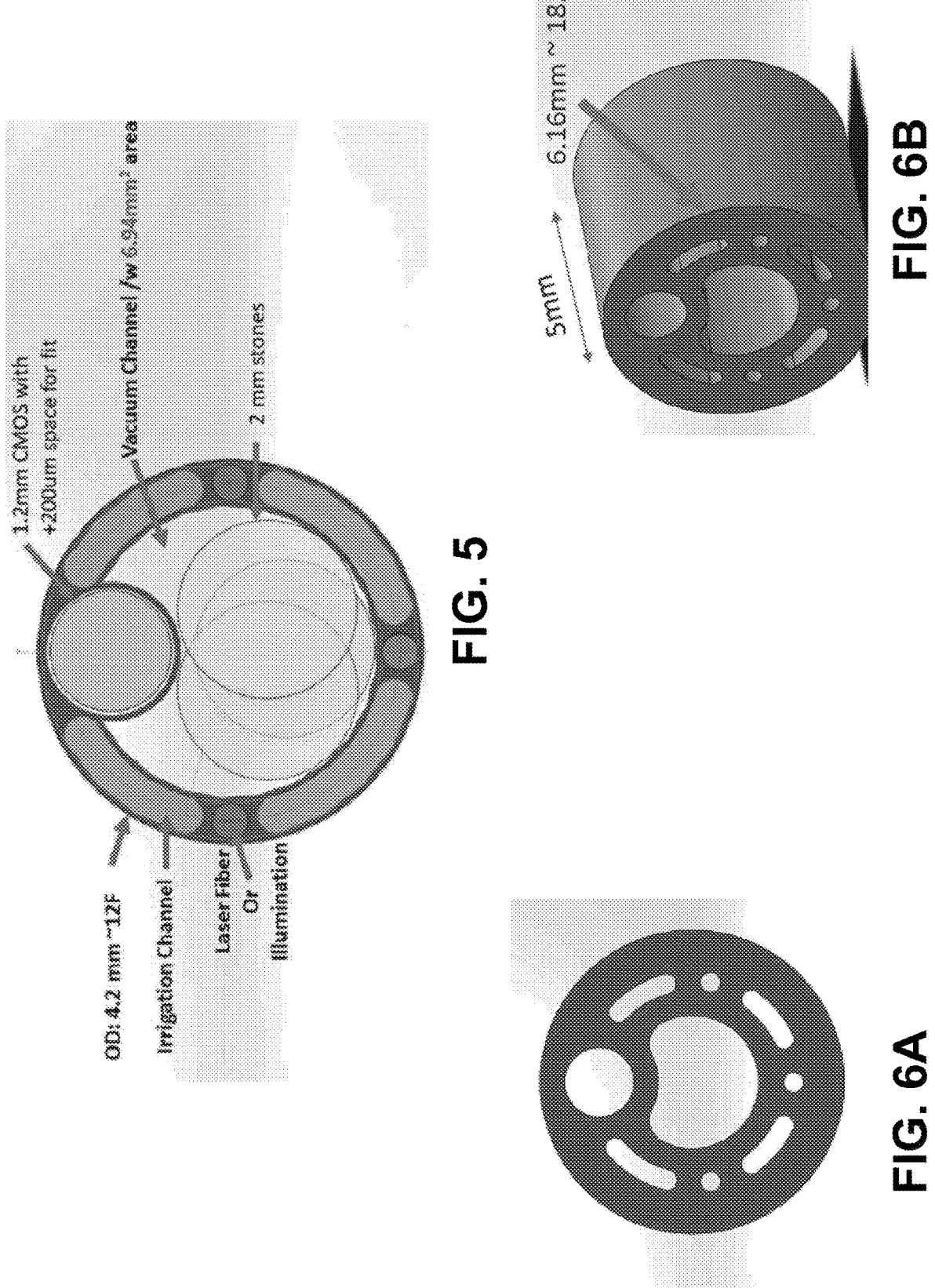
FIG. 5 depicts, in accordance with embodiments herein, an example of a larger vacuum scope with an embedded 1.2 mm CMOS.

FIGS. 6A-6B depict, in accordance with embodiments herein, an example of a 3D printed scope tip. FIG. 6A depicts a front perspective of the 3D printed scope tip. FIG. 6B depicts a diagonal perspective of the 3D printed scope tip.

FIGS. 7A-7B depict, in accordance with embodiments herein, an example of a 3D printed scope tip. FIG. 7A depicts an isometric view of the 3D printed scope tip. FIG. 7B depicts a back view of the 3D printed scope tip.

FIG. 8 shows a photograph of the endoscope tip of the present invention having stone fragments disposed within the vacuum channel adjacent to the central bar.

FIG. 9 shows a photograph of the endoscope tip of the present invention having a guide wire disposed through one of the ports of the central bar.

DETAILED DESCRIPTION OF THE INVENTION

All references, publications, and patents cited herein are incorporated by reference in their entirety as though they are fully set forth. Unless defined otherwise, technical and scientific terms used herein have the same meaning as commonly understood by one of ordinary skill in the art to which this invention belongs. Hornyak, et al., Introduction to Nanoscience and Nanotechnology, CRC Press (2008); Singleton et al., Dictionary of Microbiology and Molecular Biology 3rd ed., J. Wiley & Sons (New York, NY 2001); March, Advanced Organic Chemistry Reactions, Mechanisms and Structure 7th ed., J. Wiley & Sons (New York, NY 2013); and Sambrook and Russel, Molecular Cloning: A Laboratory Manual 4th ed., Cold Spring Harbor Laboratory Press (Cold Spring Harbor, NY 2012), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

As used herein, "treatment" or "treating" should be understood to include any indicia of success in the treatment, alleviation, or amelioration of an injury, pathology, or condition. This may include parameters such as abatement, remission, diminishing of symptoms, slowing in the rate of degeneration or decline, making the final point of degeneration less debilitating; improving a patient's physical or mental well-being; or, in some situations, preventing the onset of disease.

The terms "patient" and "subject" are used interchangeably and refer to patients and subjects of human or other mammal and includes any individual it is desired to examine or treat using the methods of the invention. However, it will be understood that "patient" does not imply that symptoms are present. Suitable mammals that fall within the scope of the invention include, but are not restricted to, primates, livestock animals (e.g., sheep, cows, horses, donkeys, pigs), laboratory test animals (e.g., rabbits, mice, rats, guinea pigs, hamsters), companion animals (e.g., cats, dogs) and captive wild animals (e.g., foxes, deer, dingoes).

As used herein, the term "fluid optical waveguide," also includes a liquid-based light waveguide.

As disclosed herein, current ureteroscopes have a working channel that is </=1.2 mm (<3.6 French) and are not equipped to provide suction evacuation of stone fragments. The small debris following laser fragmentation of a stone settles in the dependent calyces of the kidney and serves as a nidus for new stone formation, thus contributing to the recurrence of kidney stones after treatment and an ongoing cycle of treatment and recurrence. None of the currently available stone baskets can reliably remove fragments that are <1.5 mm. At this time, reliable complete stone clearance is only achieved with laparoscopic surgery, open surgery, or percutaneous stone removal; each of these is far more invasive than ureteroscopy. Thus, in accordance with an embodiment herein, the inventors have developed a universal endoscope that can serve as a ureteroscope or with a larger lumen as a nephroscope, with a specific vacuum channel that is, in some iterations, twice the size of the current working channels. This endoscope should be able to evacuate all fragments that are 2 mm or smaller.

Furthermore, as known in the art, the infection rate after ureteroscopic lithotripsy is 8.4%, with common risk factors for infection including stone size, operative duration, and retained fragments that harbor bacteria. There are also challenges concerning sterilization of the standard ureteroscope. Indeed, the sterilization process itself is injurious to the endoscope and limits its overall lifespan. There are no guidelines or quality benchmarks specific to ureteroscope reprocessing, and patient injuries and infections have been linked to the ureteroscope itself. Thus, in accordance with an embodiment herein, the invention provides a novel ureteroscope that is a disposable, single-use endoscope, thus eliminating any problems and the costs due to reprocessing.

Further, in another embodiment, the invention comprises a true wireless or modular endoscope, wherein the handle, either disposable or sterilizable, of one endoscope (e.g. ureteroscope) could be used as the handle for another endoscope (e.g. gastroscope), thus decreasing costs. Further, the currently available endoscopes are tethered to large camera towers and to bulky display screens. Thus, in accordance with various embodiments herein, a truly wireless and modular endoscope would fill this gap in technology.

In one embodiment, the present invention provides a sterile, disposable, or reusable ureteroscope that integrates, at minimum, 6 French to 21 French vacuum/working (Vacuumoscopy) channels to ensure the removal of virtually all stone particle debris at the end of laser ablation of a renal stone with a ureteroscope or percutaneous nephroscope, respectively. In another embodiment, the present invention expands indications for ureteroscopic laser stone fragmentation to stones larger than 1 cm. In another embodiment, the present invention provides a wireless and modular universal endoscope that could be used for bronchoscopy, gastroscopy, colonoscopy, and laryngoscopy to reduce costs of usability and simultaneously make endoscopy more portable.

In another embodiment, the invention will be used in all ureteroscopic or percutaneous nephrolithotomy laser lithotripsy procedures in which a kidney stone is broken into smaller fragments. Typical ureteroscopes have an approximate 1.2 mm channel that does not provide adequate suction to remove debris following stone laser fragmentation; indeed this same channel is used for irrigation for visualization and for the passage of the laser fiber itself within the kidney thereby constraining any space for fragment evacuation. These shortcomings will be overcome, in accordance with embodiments herein, by utilizing a larger bore central vacuum channel (2.5 mm or 7 French), with ongoing irrigation and laser fiber entry coming from smaller channels arrayed around the central vacuum channel. The endoscope will vary in length and diameter (French) depending upon the intended use (e.g. ureteroscopy vs. nephroscopy). During ureteroscopy procedures, visualization and manipulation of the endoscope can be achieved through an array of materials around the central vacuum channel (i.e. LED light, CCD or CMOS imaging chip, guy wires for tip deflection, irrigation channels, and field-centering angled channels for laser and stone basket use). In another embodiment, a version of the novel disposable ureteroscope would also include a unique ergonomic handle allowing for one-handed operation for advancing/retracting instruments, activating/deactivating irrigant flow, activating/deactivating suction, and a 360° thumb-driven joystick for universal tip deflection. Also, in another embodiment, the endoscope has a self-contained battery pack and is enabled for wireless communication (e.g, Bluetooth®/Wi-Fi® enabled) thereby eliminating all electrical cords and cables. In another embodiment, the suction and irrigation tubing comes off of the endoscope at 6 o'clock and directly posterior (i.e. 90 degrees to the handle), away from the surgeon's hands thereby adding to the ease of use and balance of the endoscope.

Other embodiments include a method of treating a condition or disease related to kidney stone removal in a subject, providing a device comprising a vacuumscope with a large-bore central vacuum channel, and using the device as part of the removal and/or breakdown into smaller pieces of a kidney stone in a subject. In another embodiment, the device has a self-contained battery pack. In another embodiment, the device is enabled for wireless communication (e.g. Bluetooth® and/or Wi-Fi® enabled). In another embodiment, the device is a universal endoscope. In another embodiment, the device ensures the removal of stone particle debris at the end of laser ablation of a renal stone. In another embodiment, the device provides a wireless and modular universal endoscope. In another embodiment, the device may be used for nephroscopy, bronchoscopy, gastroscopy, colonoscopy, arthroscopy, and laryngoscopy. In another embodiment, the device is used as part of a ureteroscopic and/or percutaneous nephrolithotomy procedure in which a kidney stone is broken into smaller fragments with aspiration of the fragments via the endoscope's central aspiration channel.

In another embodiment, the present invention provides a device comprising a vacuum channel adapted for a suction form of biopsy of a polyp and/or tumor in a subject. In another embodiment, the vacuum channel is adapted for suction in a colon or the upper gastrointestinal tract (i.e. esophagus, stomach, duodenum, small bowel) of a subject.

In another embodiment, the present invention provides a device, comprising a vacuumscope with a large-bore central vacuum channel. In another embodiment, the large bore central vacuum channel is about 2.5 mm to about 7 mm for a ureteroscope or nephroscope respectively. In another embodiment, the large bore central vacuum channel is about 1.5 mm to about 2.0 mm. In another embodiment, the large bore central vacuum channel is about 1.5 mm to about 8.0 mm in width. In another embodiment, further comprising ongoing irrigation coming from smaller channels arrayed around the large bore central vacuum channel. In another embodiment, the vacuumscope provides a universal endoscope handle. In another embodiment, the device is used for ureteroscopy. In another embodiment, the device is used for nephroscopy. In another embodiment, visualization and manipulation are achieved through an array of materials around the large bore central vacuum channel such as LED light, CCD or CMOS imaging chip, guy wires for tip deflection, irrigation channels, and straight or angled channels for laser and stone basket use. In another embodiment, further comprises a disposable unit. In another embodiment, the device provides a reusable ureteroscope. In another embodiment, the device provides a disposable ureteroscope. In another embodiment, the device comprises an ergonomic handle allowing for one-handed operation for advancing and/or retracting instruments, activating and/or deactivating irrigant flow, activating and/or deactivating suction, and a 360-degree thumb-driven joystick for tip deflection. In another embodiment, further comprising an endoscope with a self-contained battery pack and/or enabled for wireless communication (e.g. Bluetooth® and/or Wi-Fi® enabled) to eliminate electrical cords and cables. The vacuum channel (150) may comprise a flexible material.

In one embodiment, the present invention is a vacuum-scope comprised of two single-time use disposable or potentially reusable units, such as the large vacuum endoscope removal tip and wireless and modular battery-powered handpiece. The endoscope's shaft can vary (12 French to 26 French) with a varying central vacuum channel depending on the intended use (7 French to 21 French).

Other embodiments include a vacuumscope, comprising a large vacuum endoscope removal tip, and a wireless and modular battery-powered handpiece. In another embodiment, the large vacuum endoscope removal body (i.e. handpiece) is disposable. In another embodiment, the large vacuum endoscope removal body (i.e. handpiece) is reusable. In another embodiment, the endoscope shaft is between 12 French and 26 French and may be either disposable or reusable. In another embodiment, the vacuumscope comprises a central vacuum channel between 7 French and 21 French.

Other embodiments include an overall treatment regimen in a subject, comprising providing a device comprising a vacuumscope with a large-bore central vacuum channel, and using the device as part of a method for the removal and/or breakdown into smaller pieces of a kidney stone in a subject, wherein the method is part of a general surgical procedure on the subject.

In conjunction with various embodiments herein, devices relate generally to the medical field, and more specifically, ureteroscopy and percutaneous nephrolithotomy. However, various embodiments herein are in no way limited to only ureteroscopy, and also may be used regarding, for example, laser ablation of ureteral and renal stone, capture and removal of stone fragments, intrarenal and intraurethral surgical procedures (e.g. endoureterotomy, endopyelotomy, tumor resection), and biopsy of urothelial based renal and ureteral lesions.

The present invention features a device (100) comprising an optical instrument (120) fluidly connected to a vacuum channel (150) that is about 1.5 mm to about 8.0 mm in width. The optical instrument (120) may comprise a central bar (160) disposed at a distal end of the vacuum channel (150) across a diameter of the vacuum channel (150). The central bar (160) may divide the vacuum channel (150) to prevent clogging. In some embodiments, the vacuum channel may be about 1.5 mm to about 2.0 mm in width. The optical instrument (120) may be an endoscope, a nephroscope, a ureteroscope, or a combination thereof. The vacuum channel may be the inner part of a vacuum scope. In some embodiments, the optical instrument (120) may further comprise a plurality of irrigation channels. The plurality of irrigation channels may be arrayed around the vacuum channel and may include channels that are straight or angled. The vacuum channel may be adapted to capture a stone fragment up to 3 mm in size, a suction form of biopsy of a polyp and/or tumor in a subject, and/or suction in a bronchus, colon, or any area of the gastrointestinal tract of a subject. In some embodiments, the vacuum channel may be a large-bore central vacuum channel exiting the handle of the endoscope in a direct line.

The vacuum channel may be about 2.0 mm to about 4.0 mm for use of the device (100) as a ureteroscope. The vacuum channel is about 6.0 mm to about 8.0 mm for use of the device (100) as a percutaneous nephroscope.

In some embodiments, the optical instrument is removably attached to the distal end of the vacuum channel (150). For example, the optical instrument may be threaded onto the distal end of the vacuum channel or attached via an adhesive or welding.

In some embodiments, the optical instrument comprises a short tube with the central bar (160) disposed at a distal end of the tube. The central bar spans a diameter of the tube to bisect an opening of the tube. In some embodiments, the tube has a short length ranging from about 0.5 cm to about 2 cm. In some embodiments, the distal end of the vacuum channel may be attached to a proximal end of the tube or ring. In other embodiments, the optical instrument is flushed against the distal end of the vacuum channel. Alternatively, the optical instrument caps the distal end of the vacuum channel. In some embodiments, the optical instrument may be constructed of a polymer material, a metal, or metal alloy. In some embodiments, the vacuum channel (150) may comprise a flexible material that enables the vacuum channel (150) to flex and bend.

Visualization may be achieved through an array of optical materials located around the vacuum channel. Manipulation may be achieved through a control mechanism located around the vacuum channel. The manipulation may further comprise a magnetic guidewire steering.

In some embodiments, the device (100) may have a self-contained battery pack and may be enabled for wireless communication (e.g, Bluetooth® and/or Wi-Fi® enabled). In other embodiments, the central bar (160) may comprise one or more ports, such that one or more guidewires (104)

are disposed through the vacuum channel (150) and through the one or more ports to promote smooth controlled movement of the optical instrument (120). In some embodiments, the central bar (160) may comprise a light source (162) and/or one or more optical elements (164). The vacuum channel (150) may comprise a flexible material.

The present invention features a method of removing a biopsied tissue or stone particle or fragment thereof from an individual. In some embodiments, the method may comprise providing a device (100) comprising an optical instrument (120) operably connected to a vacuum channel that is about 1.5 mm to about 8.0 mm in width. The optical instrument (120) may comprise a central bar (160) disposed at a distal end of the vacuum channel (150) across a diameter of the vacuum channel (150). The central bar (160) may divide the vacuum channel (150) to prevent clogging. The method may further comprise removing the biopsied tissue or stone particle or fragment thereof from the individual. The biopsied tissue or stone particle or fragment thereof may be removed as part of a bronchoscopy, gastroscopy, duodenoscopy, small bowel endoscopy, colonoscopy, arthroscopy, and/or laryngoscopy procedure. The stone particle or fragment thereof may be removed as part of a ureteroscopic and/or percutaneous nephrolithotomy procedure. The vacuum channel may be about 1.5 mm to about 2.0 mm in width. Visualization may be achieved through an array of optical materials located around the vacuum channel or housed within a central bar The central bar (160) may comprise one or more ports. One or more guidewires (104) may be disposed through the vacuum channel (150) and through the one or more ports to promote smooth controlled movement of the optical instrument (120). The central bar (160) comprises a light source (162) (LEDs). The central bar (160) may comprise one or more optical elements (164), such as a CCD or CMOS chip. The vacuum channel (150) may comprise a flexible material.

The present invention features a method of performing a biopsy on a subject. The method may comprise providing a device (100) comprising an optical instrument operably connected to a vacuum channel about 1.5 mm to about 8.0 mm in width. The optical instrument may comprise a central bar (160) disposed at a distal end of the vacuum channel (150) across a diameter of the vacuum channel (150). The central bar (160) may divide the vacuum channel (150) to prevent clogging. The method may further comprise removing a biopsy sample from the subject. The sample may be a tumor and/or polyp. The vacuum channel may be about 2.0 mm to about 8.0 mm. The central bar (160), may comprise one or more ports. One or more guidewires are disposed through the vacuum channel (150) and through the one or more ports to promote smooth controlled movement of the optical instrument. The central bar (160) may comprise a light source (LEDs). The central bar (160) may comprise one or more optical elements (CMOS chip). The vacuum channel (150) may comprise a flexible material.

EXAMPLE

The following is a non-limiting example of the present invention. It is to be understood that said example is not intended to limit the present invention in any way. Equivalents or substitutes are within the scope of the present invention.

In accordance with various embodiments herein, the inventors developed a sterile, disposable, or reusable ureteroscope that integrates at minimum 6 French to 26 French vacuum/working (Vacuumoscopy) channels to ensure the removal of all stone particle debris at the end of laser ablation of a renal stone after ureteroscope (i.e. 6 F channel) or percutaneous nephrolithotomy (up to 21 F). Further, the device may expand indications for ureteroscopic laser stone fragmentation to stones larger than 1 cm. In another embodiment, the device is a wireless and modular universal endoscope that could be used for bronchoscopy, gastroscopy, colonoscopy, arthroscopy, and laryngoscopy to cut down on costs of usability and make endoscopy more portable.

In one embodiment, the invention will be used in all ureteroscopic or percutaneous nephrolithotomy laser lithotripsy procedures in which a kidney stone is broken into smaller fragments. Typical ureteroscopes have an approximate 1.2 mm channel that does not provide an adequate channel to suction and remove debris following stone laser fragmentation; indeed this same channel is used for irrigation for visualization within the kidney as well as for passage of instrumentation such as laser fibers and stone baskets. The invention will overcome such shortcomings by utilizing a larger bore central vacuum channel (2.5 mm to 7 mm) with a drainage connection exiting the back end of the endoscope such that there is no compromise to the endoscope's central vacuum channel; with ongoing irrigation coming from smaller channels arrayed around the central vacuum channel. The vacuumscope will vary in length and diameter (French) depending upon the intended use. During ureteroscopy procedures, visualization and manipulation of the endoscope will be achieved through an array of materials around the central vacuum channel (i.e. LED light, CCD or CMOS imaging chip, guide wires for tip deflection, irrigation channels, and straight/angled channels for laser and stone basket use). A version of the novel disposable ureteroscope would also include a unique detachable ergonomic handle allowing for one-handed operation for advancing/retracting instruments, activating/deactivating irrigant flow, activating/deactivating suction, and a 360° thumb-driven joystick for tip deflection. Also, the endoscope may have a self-contained battery pack and is enabled for wireless communication (e.g. Bluetooth®/Wi-Fi® enabled) thereby eliminating all electrical cords and cables. The suction and irrigation tubing comes off of the endoscope at 6 o'clock and directly posterior (i.e. 90 degrees to the handle), away from the surgeon's hands thereby adding to the ease of use and balance of the endoscope; alternatively, the suction tubing may come off the back end of the endoscope in order to facilitate aspiration of stone fragments.

In one embodiment, the vacuumscope invention is comprised of two single-time use disposable or potentially reusable units namely the large vacuum endoscope removal shaft and the wireless and modular battery-powered handpiece. The endoscope's shaft will vary (12 French to 26 French) with a varying central vacuum channel depending on the intended use (7 French for ureteroscopy to 21 French for percutaneous nephroscope).

In accordance with various embodiments herein, one may increase the range of deflective for an endoscope tip incorporating a fluid waveguide, as the fluid waveguide is more malleable than a fiberoptic light guide thereby making the tip of the endoscope easier to deflect. The liquid waveguide would, with the appropriate difference in refractive index between core and cladding, withstand a tighter bend radius than would a rigid solid such as borosilicate glass used in fiber optics. Furthermore, depending upon the variation of the two refractive indices, one could manipulate the angle at which the light energy would undergo total internal reflection that would further provide a means of increasing the range of deflective for the scope tip.

At minimum one large bore (i.e. 7 French to 21 French) vacuum port to evacuate all stone fragments <1.5 mm after ureteroscopy or larger remnants from laser lithotripsy via a percutaneous nephroscope.

Disposable thereby eliminating risks of infection or endoscope malfunction due to processing. Wireless video capabilities via Bluetooth® and/or Wi-Fi® thereby eliminating entangling cords and expensive high power light sources and fixed camera equipment. Superior universal 360-degree deflection based on joystick steering—eliminating the need for the surgeon to employ excessive wrist movement to guide the tip of the endoscope. Modular design capable of adapting various endoscope shafts to attach to the same reusable universal handle. Unique ergonomic handle design allows for single-handed control of irrigation, suction, tip deflection, and instrument projection/retraction.

Turning to FIGS. 1-9 herein in greater detail, in accordance with various embodiments herein, the inventors have developed several novels and effective versions of endoscopes with vacuum channels.

Figure 1A:
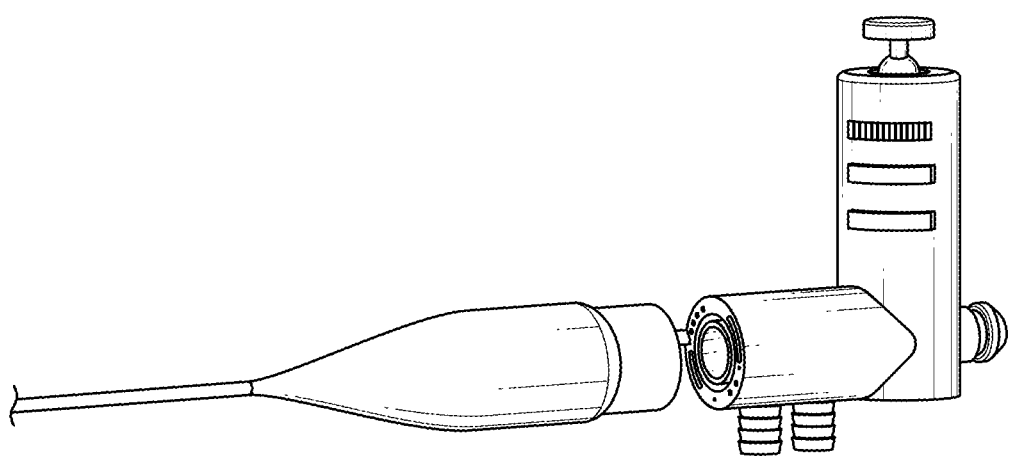
Figure 1B:
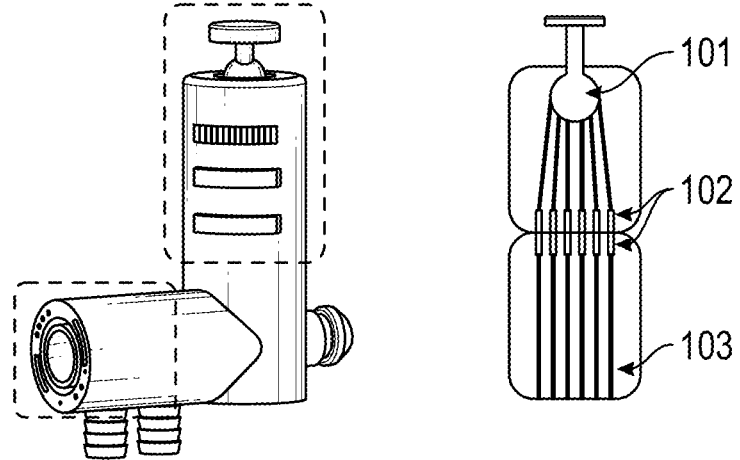
Figures 2A, 2B:
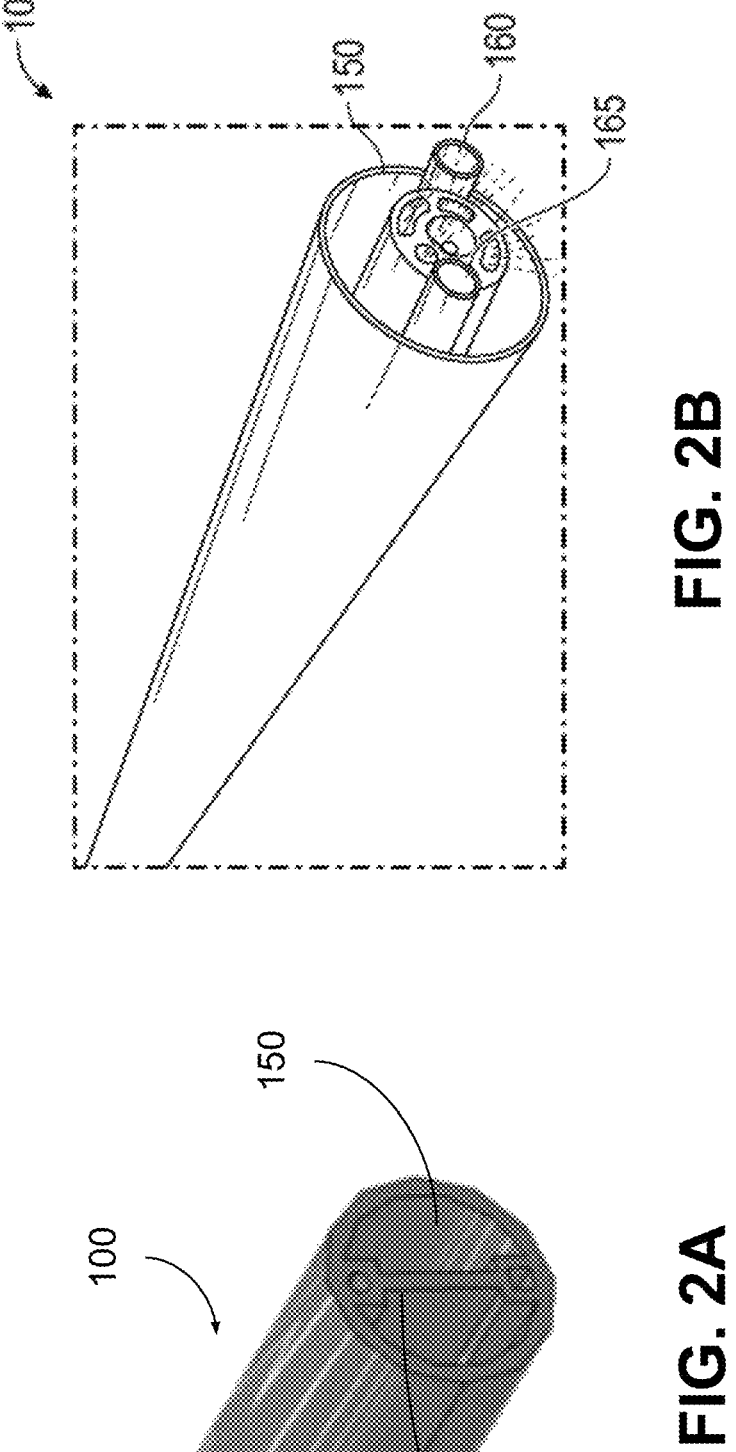
FIG. 2A depicts, in accordance with embodiments herein, an example of a 3D printed scope tip comprising a vacuum channel with a central bar disposed across a diameter of the vacuum channel.
FIG. 2B depicts, in accordance with embodiments herein, a photograph of an endoscope tip of the present invention comprising a central bar comprising multiple ports for guide wires, light source elements, and optic elements.

For example, as referenced in FIG. 2, the inventors have developed a mechanism for 360-degree actuation of a ureteroscope that allows for more intuitive navigation through the urinary tract anatomy. This mechanism involves the use of a joystick thumb control that is attached to several guy wires in the handpiece body as seen in the schematic in FIG. 2 herein. This said control mechanism (200) is coupled to detachable and disposable endoscope tips through magnets that can be seen in the schematic at the end of the handpiece. From this interface, the magnets embedded in the endoscope back end will then translate the pulling force to the distal tip of the endoscope deflecting the endoscope in the direction that tension is applied. Alternatively, in a commercially available ureteroscope, there is only a two-way actuation that provides 180 degrees of actuation. In this alternative commercially available ureteroscope, the user is forced to rotate the endoscope or supinate his/her wrist in order to steer the endoscope into the various infundibula and calyces of the renal collecting system. As referenced in FIG. 2 herein, and in accordance with various embodiments herein, the inventors have developed a design that provides a straightforward and intuitive approach to solving the problem of having to rotate the endoscope that is otherwise presented by commercially available alternatives.

Figures 3, 4:
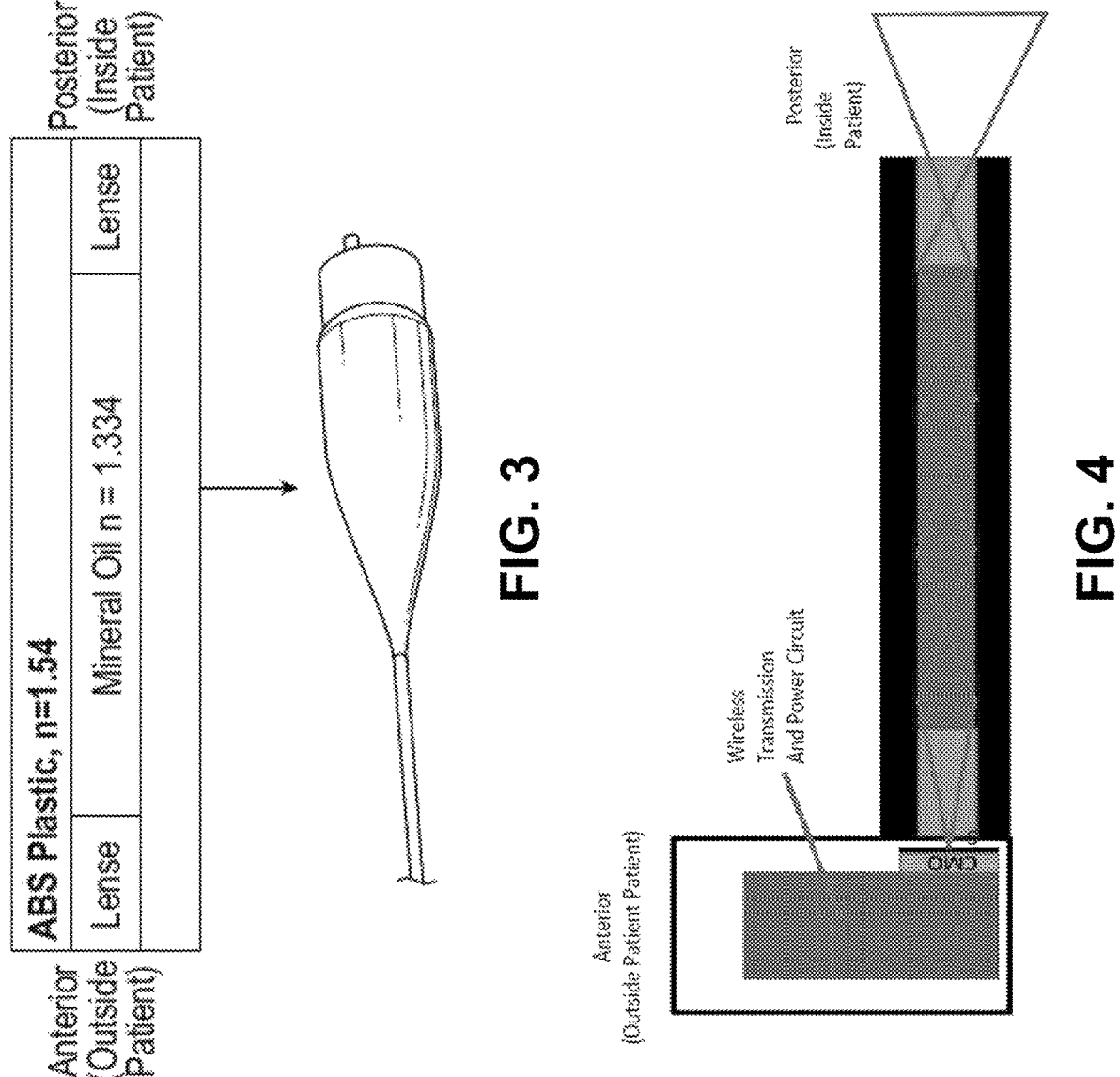
FIG. 3 depicts, in accordance with embodiments herein, a fluid optical waveguide.
FIG. 4 depicts, in accordance with embodiments herein, an example of the implementation of a fluid optical waveguide.

As referenced in FIG. 3 herein, and in accordance with various embodiments herein, the inventors have developed a vacuum ureteroscope with a plurality of mechanisms to transmit light energy, for example, either for illumination or for relaying visible light to render an image. FIG. 3 details the use of a liquid-based light waveguide, or fluid optical waveguide. Such a waveguide would transmit light energy through total internal reflection, a process governed by the change in refractive index between the waveguide and the surrounding material. At both ends of the said liquid waveguide, there will be a lens focusing optics to transmit the relayed light. In this proposed example mineral oil is shown as the inner waveguide liquid surrounded by ABS plastic. Fiber optic glass or silicon dioxide waveguides are more typical for such applications. This waveguide will permit the design of the endoscope to embody a larger suction port than typically permitted in endoscopes today. Video endoscopes port configuration is limited by the size of the CMOS chip that is present at the distal end of the scope.

As referenced in FIG. 4 herein, and in accordance with various embodiments herein, an example of an imaging system can be seen in the figure. FIG. 4 describes the implementation of the said liquid light waveguide. On the anterior portion of the device assembly, there is a CMOS or CCD imaging chip. On the distal or posterior portion of the device, there is the liquid light waveguide. The two could be coupled with a lens to focus the image relayed from the liquid waveguide to the CCD or CMOS chip in the handle. This aspect of the design provides more area on the endoscope tip for a vacuum port since the imaging aspect of the device is being moved more towards the handpiece, where there is a greater area. With a larger suction port, the device will be able to suction larger stones.

FIG. 5 herein, and in accordance with various embodiments herein, illustrates an example of a configuration of an endoscope to be used with a 1.2 mm CMOS camera on the distal end, rather than in the handle. In this example, the outer diameter of the scope is restrained to a 12-14 Fr range. This limitation is posed through the size of the ureter with an access sheath placed into the ureter; while the largest access commercially available is 16 Fr (with a 14 Fr lumen), there is the possibility that larger access sheaths may come into existence such that a 16 Fr or 18 Fr or 20 Fr ureteroscope will be used with a corresponding 18 Fr, 20 Fr, or 22 Fr ureteral access sheath. With such a geometry presented in the figure, one potential targeted stone fragment diameter that may be picked up with a ureteroscope is 2 mm, far greater than what is typically possible with conventional endoscopes given the limited size of the 1.2 mm working port. In addition, alternative commercially available endoscopes do not often provide irrigation and suction independently, which hinders the ability to catch all stone fragments efficiently as the single-channel can only be used for irrigation or suction at a given time. In the proposed endoscope, active irrigation via the outer channels can continue while suction is applied via the larger central vacuum port.

FIGS. 6A-6B and 7A-7B herein describe an example of a 3-D printed scope tip developed by the inventors. FIGS. 7A-7B depict the labeled back end of the scope tip where relevant suction and irrigation can be applied. In one embodiment, the probe tip is the most distal portion of the device, due to the impracticality of extruding tubing.

Multiple tip shapes and configurations were tested for the present endoscope invention. All tips that were tested on fragment sizes up to 1.70 mm achieved 100% clearance and no occlusions. For 1 mm obstructions, the central bar design achieved 265 mg/sec. For 2 mm obstructions, the central bar design had 100% clearance. For 2.50 mm obstructions, the central bar design encountered 4 occlusions. For 3.55 mm obstructions, the central bar design had the highest clearance (14.55%).

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features, and steps discussed above, as well as other known equivalents for each such element, feature, or step, can be mixed and matched by one of ordinary skill in this art to perform methods in accordance with the principles described herein. Among the various elements, features, and steps, some will be specifically included and others specifically excluded in diverse embodiments.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed, or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a," "an," and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are herein individually incorporated by reference in their entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting essentially of" or "consisting of", and as such the written description requirement for claiming one or more embodiments of the present invention using the phrase "consisting essentially of" or "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A device, comprising:
   an optical instrument fluidly connected to a single vacuum channel, wherein the optical instrument comprises a central bar disposed only at a distal end of the single vacuum channel across a diameter of the single vacuum channel such that the central bar divides only the distal end of the single vacuum channel into two halves to prevent clogging;
   a plurality of irrigation channels arrayed around an outer circumference of the single vacuum channel;
   an array of optical materials located around the outer circumference of the single vacuum channel for achieving visualization; and
   a control mechanism located around the outer circumference of the single vacuum channel for achieving manipulation of the optical instrument;
   wherein the central bar comprises one or more ports, a light source, and one or more optical elements;

wherein one or more guidewires are disposed through the single vacuum channel and through the one or more ports to promote controlled movement of the optical instrument.

2. The device of claim 1, wherein the optical instrument is an endoscope, a nephroscope, a ureteroscope, or a combination thereof.

3. The device of claim 1, wherein the single vacuum channel is adapted for a suction form of biopsy of a polyp and/or tumor, and suction in a bronchus, colon, or any area of a gastrointestinal tract of a subject.

4. The device of claim 1, wherein the control mechanism implements magnetic guidewire steering.

5. The device of claim 1, wherein the device is enabled for wireless communication.

6. The device of claim 1, wherein the one or more optical elements comprises a CMOS chip, a CCD chip, or a combination thereof.

7. The device of claim 1, wherein the single vacuum channel comprises a flexible material.

8. A device, comprising:

an optical instrument fluidly connected to a single vacuum channel, wherein the optical instrument comprises:

a central bar disposed only at a distal end of the single vacuum channel across a diameter of the single vacuum channel, wherein the central bar divides only the distal end of the single vacuum channel into two halves to prevent clogging, wherein the central bar comprises one or more ports, wherein one or more guidewires are disposed through the single vacuum channel and through the one or more ports to promote smooth controlled movement of the optical instrument, and wherein the central bar comprises a light source and one or more optical elements;

a plurality of irrigation channels arrayed around an outer circumference of the single vacuum channel;

an array of optical materials located around the outer circumference of the single vacuum channel for achieving visualization; and a control mechanism located around the outer circumference of the single vacuum channel for achieving manipulation of the optical instrument.

9. A method of removing a biopsied tissue or stone particle or fragment thereof from an individual, comprising:

a. providing a device comprising an optical instrument fluidly connected to a single vacuum channel, wherein the optical instrument comprises:

a central bar disposed only at a distal end of the single vacuum channel across a diameter of the single vacuum channel, wherein the central bar divides only the distal end of the single vacuum channel into two halves to prevent clogging;

a plurality of irrigation channels arrayed around an outer circumference of the single vacuum channel;

an array of optical materials located around the outer circumference of the single vacuum channel for achieving visualization; and a control mechanism located around the outer circumference of the single vacuum channel for achieving manipulation of the optical instrument;

wherein the central bar comprises one or more ports, a light source, and one or more optical elements;

wherein one or more guidewires are disposed through the single vacuum channel and through the one or more ports to promote controlled movement of the optical instrument; and b. removing the biopsied tissue or stone particle or fragment thereof from the individual.

10. The method of claim 9, wherein one or more guidewires are disposed through the single vacuum channel and through the one or more ports.

11. The method of claim 9, wherein the one or more optical elements comprise a CMOS chip, a CCD chip, or a combination thereof.

12. The method of claim 9, wherein the single vacuum channel comprises a flexible material.

* * * * *